United States Patent [19]

Backman

[11] Patent Number: 5,236,411
[45] Date of Patent: Aug. 17, 1993

[54] DEVICE FOR ELEVATING THE LIMB OF A PATIENT

[76] Inventor: Jerrold Backman, 4016 Crockers Lake Blvd. #415, Sarasota, Fla. 34230

[21] Appl. No.: 790,168
[22] Filed: Nov. 7, 1991
[51] Int. Cl.⁵ .............................................. A61F 5/00
[52] U.S. Cl. ........................................ 602/13; 602/20; 128/845; 128/DIG. 20
[58] Field of Search ................................ 602/13, 20; 128/DIG. 20, 845

[56] References Cited

U.S. PATENT DOCUMENTS

| | | | |
|---|---|---|---|
| 4,135,503 | 1/1979 | Romano | 602/13 |
| 4,340,042 | 7/1982 | Smith | 602/13 |
| 4,628,918 | 12/1986 | Johnson, Jr. | 602/13 |

FOREIGN PATENT DOCUMENTS 2619307 2/1989 France .................................. 602/20

Primary Examiner—Robert Bahr
Assistant Examiner—Lynne A. Reichard
Attorney, Agent, or Firm—Pettis & McDonald

[57] ABSTRACT

A device for elevating a limb of a patient which comprises an inflatable member that is adjustable between a deflated state and an inflated state and a harness for attaching the device to the body of a patient. The member is placed between a support surface and the limb of the patient, thus elevating the limb.

5 Claims, 3 Drawing Sheets

DEVICE FOR ELEVATING THE LIMB OF A PATIENT

RELATED DOCUMENTATION

A disclosure document No. 277518 was filed on Mar. 27, 1991 by the inventor Jerrold H. Backman.

BACKGROUND OF THE INVENTION

1. Field of the Invention

The present invention relates to a device for maintaining the limb of a patient in an elevated position. When elevating an arm, the device may be used while the patient is either mobile or stationary. When stationary the device may be placed between the arm and a support surface other than the body of the patient.

2. Description of the Prior Art

A number of splint-type devices are currently in use for immobilizing limbs of patients during the healing process or while being transported from an accident scene to a hospital. Such devices are designed to restrict movement of the injured limb and make little provision for elevation of the limb, leaving that for slings, pillows or other methods. The splints may be inflatable or may be of the type disclosed in Millikan, et al., U.S. Pat. No. 4,971,041. This patent discloses a wrap having hook and loop fasteners attached to its interior surface and to elongated tubes of cushioning material, for positioning of the cushioning material on the wrap. The limb is placed within the wrap, the elongated tubes positioned to comfortably secure the limb and then the wrap is closed to prevent further movement of the limb. This device does not provide means for elevating the limb during treatment or recuperation.

Other devices have been developed specifically for positioning a patient's limb, including placing them in elevated positions. As a part of the healing process, the body sends fluid to its injured parts. Unfortunately, the body's processes for removal of fluids are not as efficient, resulting in swelling. Failure to remove the fluids from the injury site can cause a build up in scar tissue and permanent loss of function. Elevation is the most efficient method of reducing swelling. In severe swelling, the arm must be above the heart at all times: hand above the wrist, wrist above the elbow and elbow above shoulder. This progression of elevation encourages the return of excess fluids to the bloodstream. Any restriction in the flow of fluid in the arm should be avoided, particularly constrictive straps fastened about the arm. It is also important that the joints of the limb remain free to move. Maintaining the joints in a rigid position creates stiffness within the shoulder, elbow and wrist. One device for elevating an arm is disclosed in U.S. Pat. No. 4,375,809 to Meals. This patent teaches an inflatable pillow comprised of a number of chambers. The patient's arm is placed between the chambers in a flexed position, generally at a 90° angle. The pillow must be supported by a table or other generally fixed surface restricting the mobility of the patient. In addition, the pillow has very little capability to adjust the amount of elevation to be applied to the limb.

An elevation device is also disclosed in U.S. Pat. No. 4,836,195 issued to Berrehail, which discloses a relatively rigid plate that is attached to the trunk of the patient by a belt and a shoulder strap. The plate is formed into an L-shape so that one leg of the device is placed against the body, being held in place by the belt, and the second leg extends outwardly supporting the upper arm of the patient. A second plate may be used to support the forearm and hand separately. This device does not elevate the arm sufficiently in the proper progression, is cumbersome and is difficult to adjust.

U.S. Pat. No. 4,896,660, issued to Scott discloses a device that is generally rigid and complex for elevating an arm. The upper arm support is attached by a strap to a sleeve inserted over the opposing shoulder. A second rigid support for elevating the forearm and hand is attached to the upper arm support by hook and loop fasteners. The device does not adequately elevate the arm in the proper progression, is cumbersome, and is difficult to adjust, permitting little adjustment between the upper arm and the body.

Notwithstanding the existence of such devices for elevating the arms of a patient, it remains clear that there is a need for an elevation device that has no restrictive straps about the limb, is hygienic, light weight, places the arm in the proper progression of elevation, is simple to use, inexpensive and highly adjustable. A device is needed that may be used while the patient is upright and mobile, seated or in the prone position.

SUMMARY OF THE INVENTION

The present invention relates to a device for elevating the limbs of a patient during recuperation from injury, surgery or other problems. The device is comprised of an inflatable member that is adjustable between a deflated state and an inflated state. The member is placed between a support means and the limb of a patient so that the limb is elevated above the support means to the required position by inflating or deflating the member. The member is preferably attached to the body of the patient by a harness so that the side of the body under the arm of the patient provides the necessary support means. The member may also be placed on a table, chair arm, bed or other similar structure to provide the appropriate support.

The harness is slidably attached to the member to ensure flexibility and adjustment. The harness is also fully adjustable to permit wearing by patients of differing stature.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
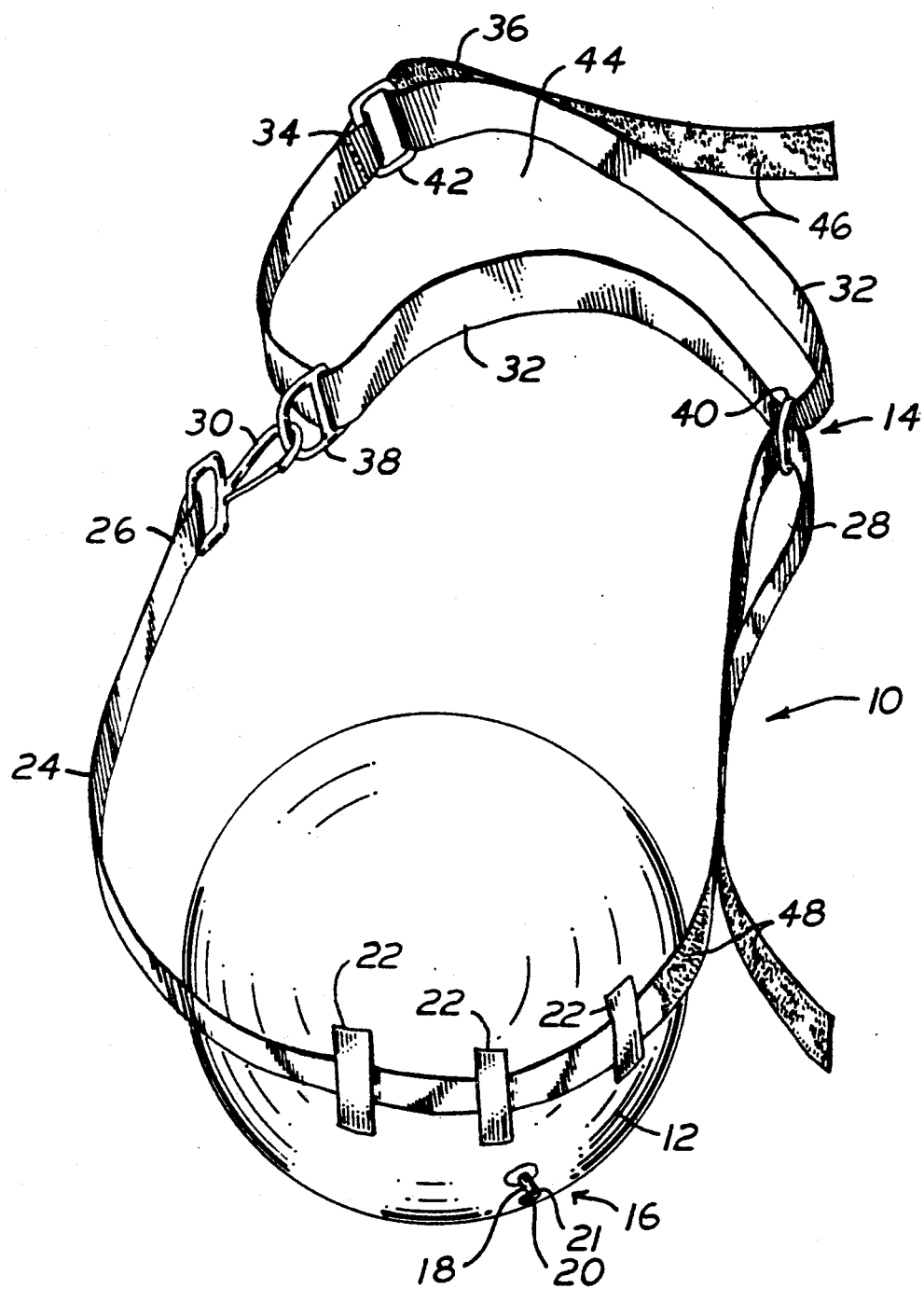
FIG. 1 is a perspective view of a preferred embodiment of the limb elevating device.

A preferred embodiment for the limb elevating device is illustrated in the drawing FIGS. 1-5 with the device generally indicated as 10. Referring first to the view of FIG. 1, it can be seen that the limb elevating device 10 is comprised of an inflatable member 12 and a harness shown generally as 14.

The hollow inflatable member 10 is adjustable between a deflated state and an inflated state by adding and subtracting air through an inflating and deflating means, conveniently an air valve shown generally as 16 in FIG. 1. In the preferred embodiment, the air valve 16 comprises a tube 18 that is in fluid flow communication with the hollow interior of member 12. A plug 20, being attached to tube 18, is removably insertable into the open end 21 of the tube 18 to seal the air valve 16. In the preferred embodiment, member 12 is hollow, having a thin, flexible outer shell, and when fully inflated has a generally spherical shape. As the member 12 is deflated by removing the plug 20 and allowing air to escape, the member becomes flattened and loses is spherical shape. While in the preferred embodiment, member 12 is spherical when fully inflated, other embodiments may have other shapes suitable for elevating a limb. Member 12 is made from rubber, plastic or other suitable air tight materials necessary to prevent the loss of air. In the preferred embodiment, the air tight shell is covered by a layer of breathable and absorbent cloth (not shown) for comfort during use.

A harness 14 is used to position and attach member 12 to the body of a patient so that the member 12 is adjacent to the limb to be elevated, as shown in FIGS. 2-5. It can be seen more clearly in FIG. 1 that the harness 14 in the preferred embodiment is comprised of three loops 22 attached to member 12 generally along an equatorial circumferential line when the member 12 is fully inflated as a sphere. The loops 22 may be heat sealed, glued to member 12, sewn to the outer fabric, or attached by any other appropriate means depending upon the material from which member 12 is constructed. In the preferred embodiment, in which the member 12 has a 12-14 inch diameter, the loops 22 are spaced generally five inches apart; however, to increase stability they may be spaced apart approximately seven inches, and to increase maneuverability the spacing may be reduced to approximately three inches. The preferred spacing for any given size member is one-eighth of the circumference of member 12 with an acceptable range between one-twelfth and one-fifth of the circumference. The loops 22 are sized to receive a first flexible strap 24.

The first flexible strap 24 has a first end segment 26 and a second end segment 28. The first strap 24 is slidably inserted through each loop 22 so that the first end segment 26 and the second end segment 28 extend beyond opposing sides of member 12. The first end segment 26 has a hook 30 attached thereon. The hook 30 in the preferred embodiment is a self-closing hook to prevent unintentional disengagement. A flexible second strap 32 having a first end portion 34 and a second end portion 36 is attached to the first strap 24 by a first ring 38 and a second ring 40 that are slidably attached to the second strap 32.

The second strap 32 is attached to the first strap 24 by attaching the hook 30 to the first ring 38 and by passing the second end segment 28 through ring 40 and folding it back upon itself, where it is attached to the first strap 24 by an attaching means, conveniently a hook and loop fastener 48.

A third ring 42 is attached to the first end portion 34 of the second strap 32 and the second end portion 36 is passed through the third ring 42 and folded back upon itself to form a loop defining an opening 44 therethrough. The second end portion 36 is attached to the second strap 32 by a fastening means, conveniently a hook and loop fastener 46. In the preferred embodiment, hook and loop fasteners were used for both the fastening means and the attaching means; however, buckles, clasps, snaps and other similar structures may be used as well.

In the preferred embodiment, the straps are constructed of woven nylon material approximately one inch in width. Any suitable material may be substituted, including, but not restricted to, other woven materials, vinyl or leather. First strap 24 is generally one inch wide in the preferred embodiment to provide the appropriate amount of support for member 12, and at the same time permitting adjustability and flexibility in the movement of member 12 about and on the first strap 24 and about the side and the arm of the patient's body. Other widths may be used for the first strap 24, making the strap either wider to provide increased support for member 12 or narrower so that member 12 may move about the strap 24 more easily. The second strap 32 is also one inch wide but may be increased in width in those areas that contact the body for increased comfort. The first ring 38, the second ring 40 and the third ring 42 are all sized to receive the second strap 32 and are constructed of metal, plastic or any other suitable material.

Figure 2:
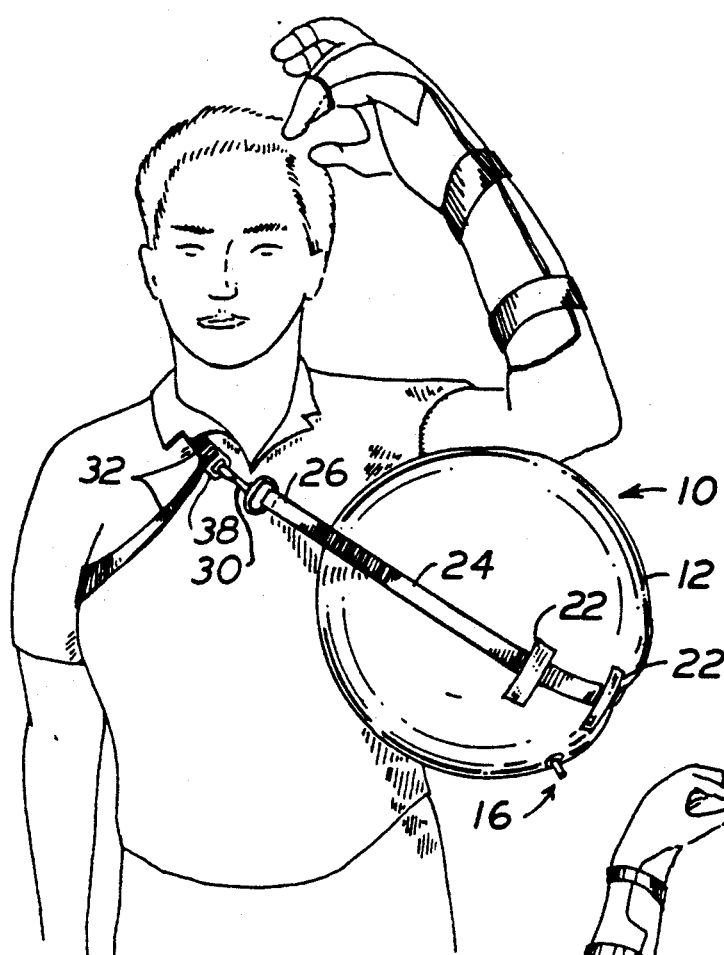
FIG. 2 is a front side elevation of the limb elevating device illustrating the attachment of the device to the body of a person.
Figure 3:
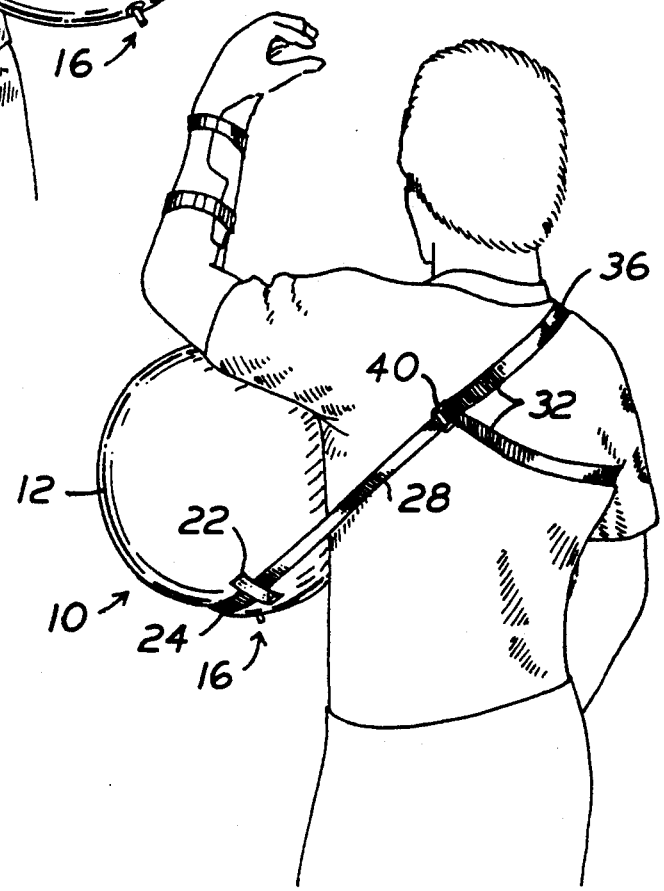
FIG. 3 is a rear side elevation of the limb elevating device shown in FIG. 2.

Having thus set forth a preferred construction for the device 10 for elevating the limb of a patient, it is to be remembered that this is but a preferred embodiment. Attention is now invited to a description of the use of device 10 for elevating an injured limb. In order to elevate the left arm of a patient, as shown in FIGS. 2 and 3, the device is assembled as shown in FIG. 1 with member 12 partially inflated. The hook 30 is disengaged from the first ring 38 and member 12 is placed snugly between the patient's upper arm and the side of the patient's body. Member 12 is oriented so that the loops 22 are facing away from the side of the patient's body and thus member 12 is interposed between the first strap 24 and the body of the patient. The first end segment 26 of the first strap 24 is held adjacent to the ball and toward the front of the patient. The first ring 38 is then grasped from behind the patient so that the second end segment 28 of the first strap 24 is wrapped around the back of the patient and the second strap 32 is brought around the right-hand side to the front of the patient. The patient then places his right arm and head through the opening 44 so that the second strap 32 rests alongside the right side of the patient's neck. The other portion of the second strap 32 will then be located under the patient's right arm. Now, the first ring 38 may be reattached to the hook 30. The second end segment 28 and the second end portion 36 are adjusted by the attaching means 48 and the fastening means 46 respectively to insure that the harness 14 and member 12 fits snugly but comfortably. The height at which the arm is raised can then be adjusted by increasing or decreasing the amount of air contained within member 12. This is done by removing the plug 20 from the tube 18 of the air valve 16, blowing into the tube 18 to add air or allowing the air to escape to remove air. Further, increases or decreases in elevation can be obtained by rotating member 12 toward the arm creating a cam-like action between member 12 and the side and arm of the patient. The arm is now elevated above the heart in the proper progressive rate of elevation; the patient's hand above the wrist, wrist above the elbow, and elbow above the shoulder. Straps are not used about the arm to avoid any constriction in the movement of the fluids from the site of the swelling. By not using straps or other restraints about the arm, movement is permitted in those joints not restrained by casts or other means. That movement reduces stiffening of the joints.

Figure 4:
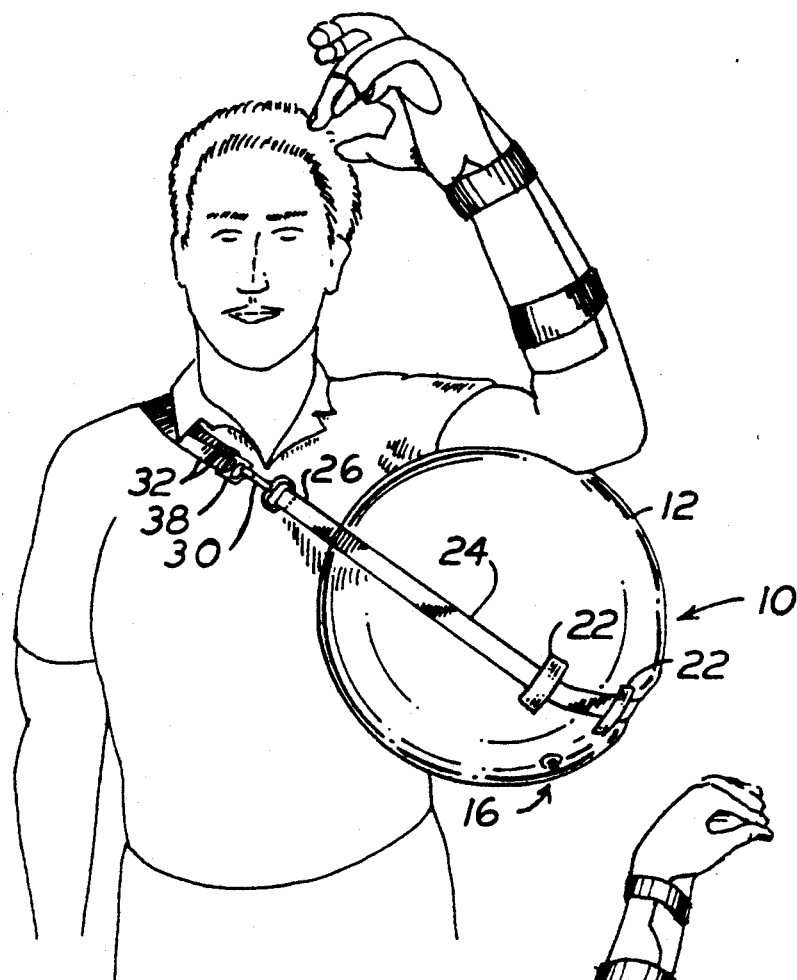
FIG. 4 is a front side elevation of the limb elevating device illustrating the harness used as a single strap when attaching the device to the body of a person.
Figure 5:
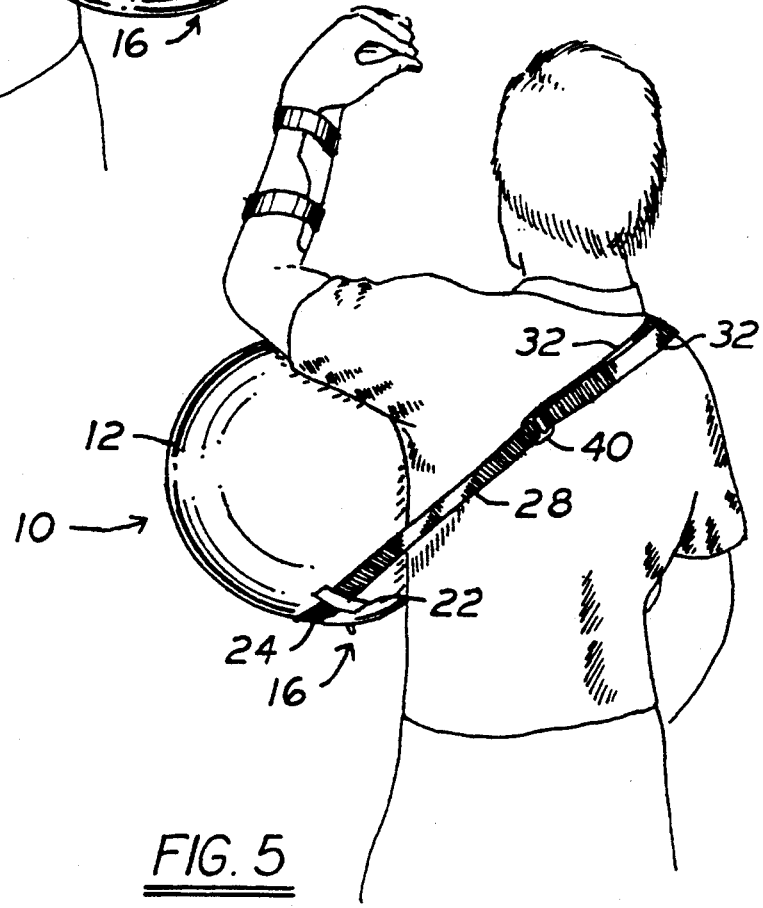
FIG. 5 is a rear side elevation of the limb elevating device shown in FIG. 4.

FIGS. 2 and 3 demonstrate the positioning on the patient for an injured left arm or hand. If it were the right arm or hand that were injured, the harness 14 would be attached in a similar fashion, but with the member 12 under the right arm. FIGS. 4 and 5 illustrate that the harness 14 could be a single strap or, as in the case of FIGS. 4 and 5, both portions of the second strap 32 may be placed about the patient's neck to form a single strap.

It will thus be seen that the objects set forth above among those made apparent from the preceding description, are efficiently attained and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A device for elevating a limb of a patient, said device comprising:
    a generally spherical inflatable member, adjustable between a deflated state and an inflated state, said member adapted for placement between a support means and the limb of a patient whereby said member elevates the limb of the patient;
    an attaching means comprising at least one loop attached to said member and a harness comprising a first strap slideably received by said loop and a second strap slideably attached to said first strap such that said first and second straps are adapted to circumferentially pass about the trunk of the patient; and
    means for adjustably inflating and deflating said member.

2. A device for elevating an injured limb of a patient as in claim 1 wherein said harness further comprises:
    a first ring, a second ring and a third ring, said first and said second rings each being slideably attached to said second strap, said second strap having a first end portion and a second end portion, said third ring being attached to said first end portion of said second strap, said second end portion of said second strap being passed through said third ring, and said second end portion of said second strap being adjustably attached to itself by a fastening means; and
    said first strap having a first and a second end segment, said harness further comprising a hook attached to said first end segment of said first strap, said hook being removably attached to said first ring; and said second end segment of said first strap being passed through said second ring and then folded back upon itself and removably and adjustably attached to itself by an attaching means, such that said second strap is attached to said first strap.

3. A device for elevating an injured limb of a patient as in claim 1 wherein said attaching means comprises three retaining loops, and said first strap is slideably inserted through said three loops.

4. A method for elevating an injured arm of a patient by utilizing an inflatable member that is adjustable between a deflated state and a generally spherical inflated state, and two straps for attaching the member to the body of a patient, comprising the steps of:
    a. slideably attaching said first strap to said member;
    b. slideably attaching said second strap to said first strap;
    c. positioning said member between an upper portion of the injured arm of the patient and a side of the body adjacent the injured arm of the patient;
    d. placing said first and said second straps circumferentially about the body of the patient and adjusting said straps so that said member is held under the upper portion of the injured arm of the patient; and
    e. adjusting the amount of fluid contained within said member, thereby elevating the injured arm to a predetermined position.

5. A device for elevating an injured arm of a patient, said device comprising:
    an inflatable member, adjustable between a deflated state and an inflated state, said member adapted for placement between a side of the body adjacent the injured arm and an upper portion of the injured arm of the patient, whereby said member elevates the injured arm of the patient;
    an attaching means comprising at least one loop attached to said member;
    a harness comprising a first flexible strap slideably received by said loop and a second flexible strap, a first ring and a second ring each slidably attached to said second strap, said second strap comprising a first end portion and a second end portion, a third ring attached to said first end portion of said second strap, said second end portion of said second strap being passed through said third ring, and said second end portion of said second strap being adjustably attached to itself by a fastening means; and
    said first strap having a first and a second end segment, said harness further comprising a hook attached to said first end segment of said first strap, said hook being removably attached to said first ring; and said second end segment of said first strap being passed through said second ring and then folded back upon itself and removably and adjustably attached to itself by an attaching means, such that said second strap is attached to said first strap, such that said first and second straps are adapted to circumferentially pass abut the truck of the body of the patient to maintain said member between a side of the body adjacent the injured arm and an upper portion of the injured arm of the patient; and
    means for adjustably inflating and deflating said member.

* * * * *

UNITED STATES PATENT AND TRADEMARK OFFICE
CERTIFICATE OF CORRECTION

PATENT NO. : 5,236,411
DATED : August 17, 1993
INVENTOR(S) : Jerrold Backman It is certified that error appears in the above-identified patent and that said Letters Patent is hereby corrected as shown below:

In the CLAIMS:

Claim 5, column 6, line 60, "abut" should be --about--;

Claim 5, column 6, line 60, "truck" should be "trunk".

Signed and Sealed this

Eighteenth Day of October, 1994

*Attest:*

BRUCE LEHMAN

*Attesting Officer*     *Commissioner of Patents and Trademarks*